United States Patent [19]
Honzawa et al.

[11] Patent Number: 5,523,845
[45] Date of Patent: Jun. 4, 1996

[54] A FIBER OPTIC DEVICE FOR MEASURING LIQUIDS WHICH ARE DRAWN INTO AN END OF THE DEVICE TO A PREDETERMINED DISTANCE FROM THE END OF THE OPTICAL FIBERS

[75] Inventors: Katsu Honzawa; Kazuhiro Atsumi; Humihiko Shimomura, all of Hamamatsu; Seiji Kawaguchi, Ayase; Yuichiro Sakamoto; Hisaya Motojima, both of Tokyo; Masayuki Masuko; Tsuyoshi Hayakawa, both of Hamamatsu, all of Japan

[73] Assignee: Biosensor Laboratories Co., Ltd., Tokyo, Japan

[21] Appl. No.: 378,369

[22] Filed: Jan. 25, 1995

[30] Foreign Application Priority Data

Feb. 4, 1994 [JP] Japan ................... 6-012654

[51] Int. Cl.⁶ .................. G01N 21/11; G01N 21/64; G01N 21/65
[52] U.S. Cl. .............. 356/440; 250/227.23; 356/301; 385/12
[58] Field of Search ................. 356/440, 301; 385/12; 250/227.18, 227.23

[56] References Cited

U.S. PATENT DOCUMENTS 3,814,081 6/1974 Mori .................. 385/12 X
4,622,974 11/1986 Coleman et al. ............ 356/440 X
4,757,194 7/1988 Simms ................ 250/227.21

FOREIGN PATENT DOCUMENTS 038912 11/1981 European Pat. Off. .
076406 4/1983 European Pat. Off. .
62-501102 4/1987 Japan .
346564 2/1991 Japan .

OTHER PUBLICATIONS

Patent Abstracts of Japan, vol. 10, No. 327 (P–513) [2383] 7 Nov. 1986 JP–A–61134648 Jun. 1986.

*Primary Examiner*—Vincent P. McGraw
*Attorney, Agent, or Firm*—Sughrue, Mion, Zinn, Macpeak & Seas

[57] ABSTRACT

The first branch 1a of the optical fiber 1 is connected to the light source 2, and the second branch 1b is connected to the optical measuring unit 3. A taper-shaped tip member 8 is fitted to a tip end of the optical fiber unit 1 with the use of a jig member 4. The inner hollow space 7 in the tip member 8 is connected with the air suction device 11, through the gap 5 formed between the optical fiber unit 1 and the jig member 4 and the air suction tube 10. The air suction device 11 discharges air from the inner hollow space 7 to suck liquid through the through-hole 6 into the inner hollow space. The air suction device 11 is controlled by the controller 12. Because the optical fiber unit can directly irradiate liquid with light, measurement can be performed with high sensitivity. The optical fiber unit is prevented from contamination.

11 Claims, 2 Drawing Sheets

A FIBER OPTIC DEVICE FOR MEASURING LIQUIDS WHICH ARE DRAWN INTO AN END OF THE DEVICE TO A PREDETERMINED DISTANCE FROM THE END OF THE OPTICAL FIBERS

BACKGROUND OF THE INVENTION

1. Field of the Invention

The present invention relates to a device for measuring optical characteristics of various kinds of liquid analyte with the use of an optical fiber. This device can measure the amount of light absorbed or scattered by a liquid analyte and can measure the amount of light fluorescently or chemically emitted from the liquid.

2. Description of the Related Art

Conventionally, there are two methods for measuring, with the use of an optical fiber, the amount of light fluorescently or chemically emitted from a liquid analyte. In one method, one end of the optical fiber is immersed directly into a liquid held in a vessel so as to irradiate the liquid with detection light. In the other method, an optically transparent container is additionally provided. A liquid analyte from the vessel is first transferred to the optically transparent container and then irradiated with detection light through the transparent wall of the container.

In the first method, the optical fiber is contaminated by the liquid. Although the second method eliminates contamination of the optical fiber, measurements are insufficiently accurate. Because the optical fiber is separated from the liquid by the thickness of the container wall, less light reaches the optical fiber, thereby lowering efficiency at which light is picked up.

SUMMARY OF THE INVENTION

It is therefore, an object of the present invention to overcome the above-described drawbacks, and to provide a device that can directly irradiate liquid with light from an optical fiber and directly pick up light from the liquid by the optical fiber to enhance measurement accuracy while preventing the optical fiber from being contaminated with the liquid.

In order to attain the object and other objects, the present invention provides a device for measuring optical characteristics of liquid, comprising: an optical fiber unit having a detection end and a first end opposed to each other; a tip member mounted on the detection end of the optical fiber unit for being immersed into liquid to be detected, the tip member having a wall defining an inner hollow space, into which the detecting end of the optical fiber unit being exposed, and defining a through-hole communicated with the inner hollow space; an air suction unit connected with the inner hollow space of the tip member for discharging air out of the inner hollow space, to thereby suck a proper amount of the liquid through the through-hole into the inner hollow space, the optical fiber unit receiving, at the detecting end, light emitted from the liquid thus held in the inner hollow space and guiding the light from the detecting end toward the first end; and an optically-measuring unit connected to the first end of the optical fiber unit for receiving the light guided to the first end and for measuring the light, to thereby measure optical characteristics of the liquid.

BRIEF DESCRIPTION OF THE DRAWINGS

The above and other objects, features and advantages of the invention will become more apparent from reading the following description of the preferred embodiment taken in connection with the accompanying drawings in which.

DETAILED DESCRIPTION OF THE PREFERRED EMBODIMENT

Figure 1:
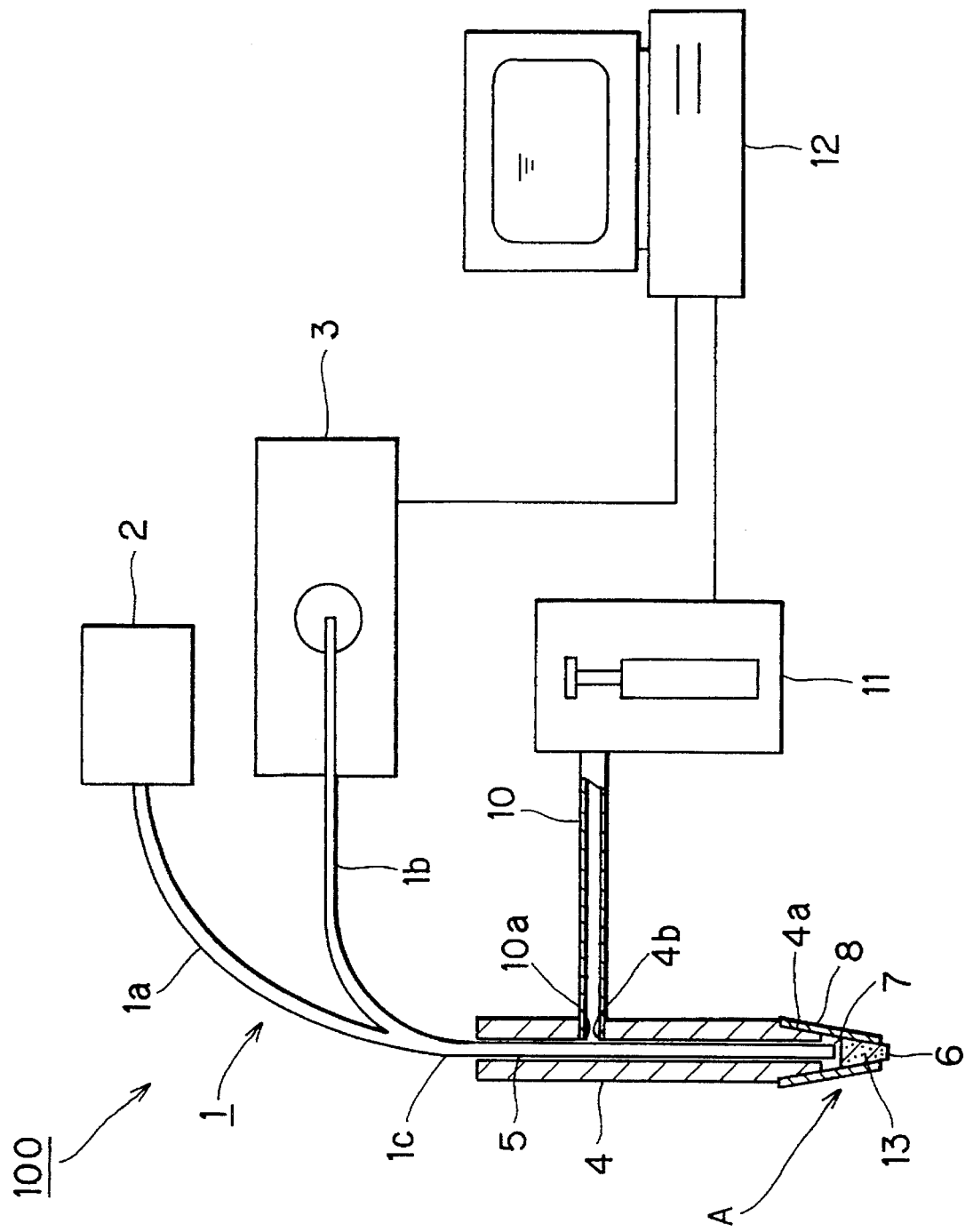
FIG. 1 is a schematic illustration showing a device for optically measuring liquids of an embodiment according to the present invention.
Figure 2:
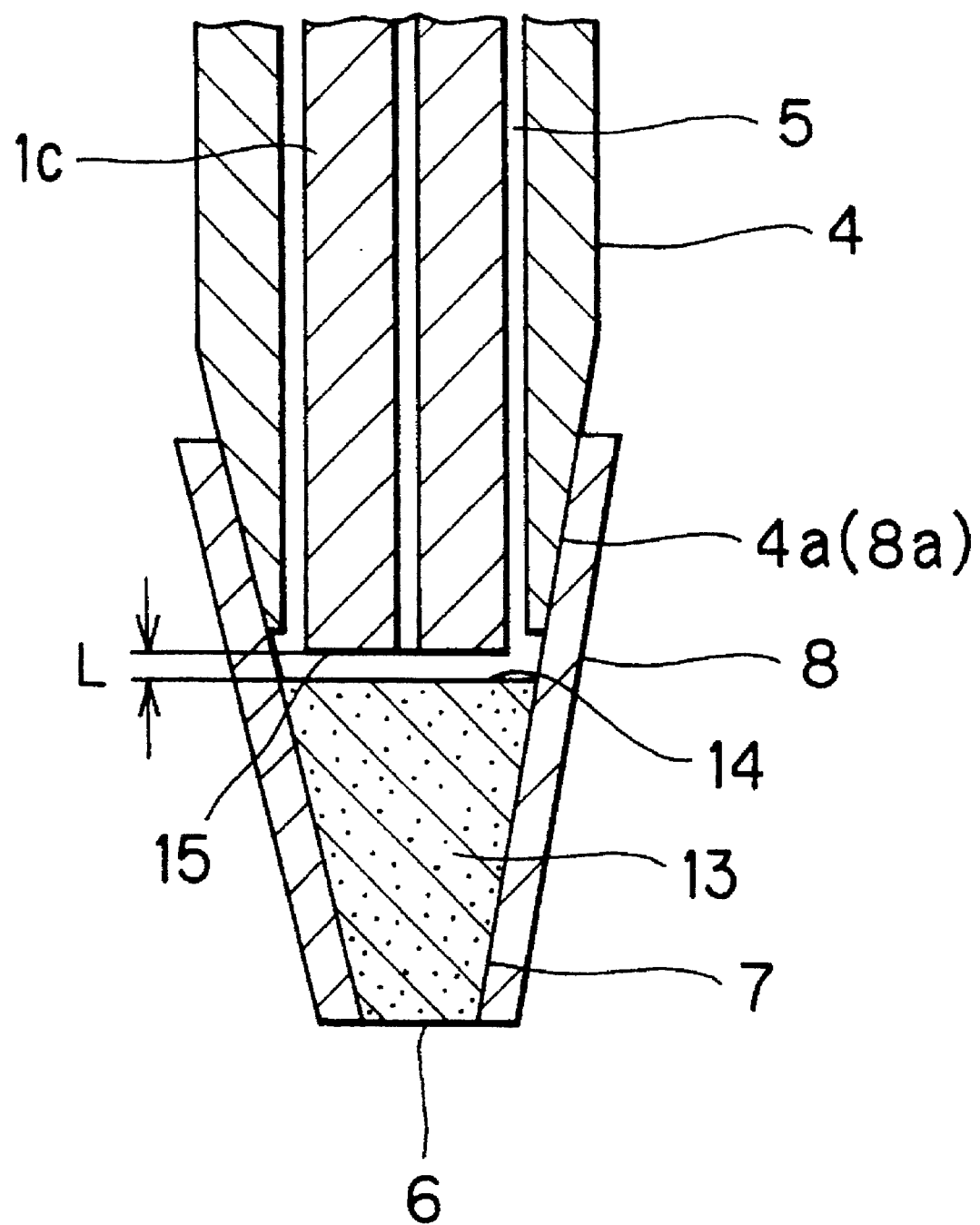
FIG. 2 is a enlarged view of a part A in FIG. 1.

A device for optically measuring liquids according to a preferred embodiment of the present invention will be described while referring to the accompanying drawings wherein like parts and components are designated by the same reference numerals as those shown in FIGS. 1 and 2 to avoid duplicating description.

The device 100 for optically measuring liquids of the embodiment includes an optical fiber unit 1 constructed from a pair of optical fibers. Each of the optical fibers has a diameter in the range of 3 mmφ and 7 mmφ. The two optical fibers are connected along end sections to form a Y-shaped unit consisting of a trunk portion 1c and a first and second branch portions 1a and 1b. The trunk portion 1c is formed from the connected lengths of the two optical fibers. A detection end 15 forms the tip of the trunk portion 1c opposite the fork of the Y shape. The first and second branch portions 1a and 1b are formed from the unconnected lengths of the optical fibers. The first branch portion 1a is connected to a light source 2, such as a xenon lamp and a halogen lamp. The light source 2 is for emitting excitation light of wavelength in the range of 250 nm and 1800 nm. The second branch portion 1b is connected to an optical measuring unit 3, such as a photon counter and a photon multi-channel analyzer. The optical measuring unit 3 is for measuring the amount of scintillation light emitted from liquid analyte upon excited with the excitation light, as will be described later.

A tubular jig 4 is provided mounted on the trunk portion 1c so that a gap 5 is produced between the narrower outer periphery of the trunk portion 1c and the larger inner periphery of the tubular jig 4. The jig 4 is fixedly secured to the trunk portion 1c. The end of the jig 4 near the detection end 15 of the trunk portion 1c is tapered, thereby forming a tapered portion 4a.

A tip member 8 is fitted to the tubular jig 4. The tip member 8 has a tapered wall 8a enclosing an inner hollow space 7. A tip end of the tapered wall 8a is formed with a through-hole 6 in communication with the inner hollow space 7. The tip member 8 is securely fitted to the jig 4 in such a manner that the tapered wall 8a is adhered to the tapered portion 4a. This configuration leaves the detection end 15 of the optical fiber unit 1 exposed in the inner hollow space 7.

The tubular jig 4 has a through-hole 4b at a predetermined position on the peripheral wall. One end 10a of an air suction tube 10 is fitted to the through-hole 4b so as to be fluid communication with the gap 5. An air suction device 11 such as an air discharge pump is connected to the other end of the air suction tube 10.

A controller 12 such as a microcomputer is connected to the air suction device 11 for driving the air suction device 11. The controller 12 controls air suction volume, air suction speed, and timing at which the air suction starts and stops. The controller 12 is connected also to the optical measuring unit 3 for receiving measured results and for calculating optical characteristics of the liquid analyte based on the measured results.

To measure optical characteristics of liquid analyte with the device 100 constructed as described above, the jig member 4 is located upright in a vessel, in which liquid analyte is held, so that the tip end of the cone-shaped tip member 8 faces downwardly. In this condition, the detecting end 15 is positioned above the through-hole 6. Then, the tip member 8 is immersed in the liquid, until the through-hole 6 nearly contacts the surface of the liquid.

Then, the controller 12 starts driving the air suction device 11 to discharge or draw air from the inner hollow space 7 through the Gap 5 and the air suction tube 10. This produces a negative pressure inside the inner hollow space 7, which in turn sucks, through the through-hole 6, an amount of liquid 13 required for measurement. The controller 12 controls the air suction device 11 to suck an amount of air at a speed sufficient to raise the level 14 of the liquid 13 in the inner hollow space 7 until quite close to but not in contact with the surface of the detection end 15. For example, controlling the air suction amount in a range of 100 μL to 1 mL and the air suction speed of 0.1 mL per seconds can suck the liquid 13 until its surface 14 reaches the level lower than the detection end 15 by a distance L of about 3.0 mm or less.

Although not shown in the drawings, a liquid level sensor may be additionally provided in the inner hollow space 7. The liquid level sensor is for outputting a signal indicative of the level of liquid sucked into the inner hollow space 7. The controller 12 can regulate drive of the air suction device 11 based on the signal.

When the liquid is properly sucked into the tip member 8, the light source 2 starts emitting excitation light. The excitation light is guided by the first branch portion 1a and the trunk portion 1c to be radiated from the detection end 15 onto the liquid 13 held in the tip member 8. The liquid 13 emits scintillation light when excited with the excitation light. The scintillation light is then received by the detection end 15. The scintillation light is guided by the trunk portion 1c and the second branch portion 1b. The optical measuring unit 3 receives the scintillation light emitted from the end of the branch portion 1b.

It is noted that the detecting end 15 receives not only the scintillation light but also some amounts of excitation light that is reflected from and scattered by the liquid 13. The measuring unit 3 includes a wavelength selector, such as an interference filter and a spectrometer, for separating the scintillation light from the excitation light. In the optical measuring unit 3, therefore, the scintillation light is separated from the excitation light before being measured. Thus, only the desired information on the scintillation light emitted from the liquid 13 is obtained.

The controller 12 automatically controls the above-described series steps of operation: the liquid sucking step; the excitation light irradiating step; and the scintillation light measuring step. Simultaneously with these operations, the controller 12 displays and records the measured results.

As described above, according to the present invention, the level 14 of the liquid 13 can be finely adjusted very close to but not in contact with the detecting end 15 of the optical fiber unit. It is therefore possible to reliably detect scintillation light emitted from the liquid with high sensitivity while preventing the optical fiber unit from being contaminated by the liquid analyte.

While the invention has been described in detail with reference to the specific embodiment thereof, it would be apparent to those skilled in the art that various changes and modifications may be made therein without departing from the spirit of the invention.

For example, in the above-described embodiment, the gap 5 for sucking the liquid into the inner hollow space 7 is formed between the outer periphery of the optical fiber unit 1 and the inner periphery of the tubular jig 4. However, the gap may be formed by other various methods. For example, the optical fiber unit 1 may be made from a bundle of a plurality of optical fibers. The gaps formed between the plurality of optical fibers may be used for sucking the liquid into the inner hollow space 7. Alternatively, the air suction tube 10 may be directly connected to the inner hollow space 7. In this case, the gap 5 may be omitted.

In the present embodiment, the wavelength of the scintillation light is selected in the measuring unit 3. By also selecting the wavelength of the excitation light, the excitation light can be separated from the scintillation light to be measured by the optical measuring unit 3. In this case, the device of the present invention serves as a turbidimeter.

As described above, according to the present invention, the tip member is immersed in a liquid analyte. The air suction unit is driven to discharge air out of the inner hollow space of the tip member, thereby sucking liquid into the tip member through the through-hole. Driving of the air suction unit stops when the surface level of the liquid in the inner hollow space of the tip member reaches a position that is apart from the surface of the detecting end of the optical fiber with a predetermined small distance. Then, the liquid thus held in the tip member is optically detected by the detecting end of the optical fiber.

Thus, the optical fiber can directly irradiate the liquid with the excitation light and also can directly pick up light emitted from the liquid as excited with the excitation light. The optical fiber can therefore high-efficiently pick up light emitted from the liquid to thereby detect the light with high sensitivity. Because the end surface of the optical fiber unit is located very close to but not in contact with the liquid level, the optical fiber can be prevented from being contaminated by the liquid. Drawing or discharging air from the inner hollow space of the tip member, which is fitted to the tip end of the optical fiber unit, can easily perform fine adjustment of the distance or gap between the level of the liquid sucked into the inner hollow space and the detecting end surface of the optical fiber. When desiring to promote reaction in the liquid for measuring a predetermined substance contained in the liquid, control of the liquid sucking speed can attain an optimum condition for the promotion.

What is claimed is:

1. A device for measuring optical characteristics of liquid, comprising:

an optical fiber unit having a detection end and a first end opposed to each other;

a tip member mounted on the detection end of the optical fiber unit for being immersed into liquid to be detected, the tip member having a wall defining an inner hollow space, into which the detecting end of the optical fiber unit is exposed, and defining a through-hole communicated with the inner hollow space;

an air suction unit connected with the inner hollow space of the tip member for discharging air out of the inner hollow space, to thereby suck a proper amount of the liquid through the through-hole into the inner hollow space, the air suction unit including a sucking condition control unit which controls a surface level of the liquid sucked into the inner hollow space to reach a position spaced apart from the detecting end of the optical fiber unit by a small amount of gap, the optical fiber unit receiving, at the detecting end, light emitted from the liquid thus held in the inner hollow space and guiding the light from the detecting end toward the first end; and an optically-measuring unit connected to the first end of the optical fiber unit for receiving the light guided to the first end and for measuring the light, to thereby measure optical characteristics of the liquid.

2. A device of claim 1, further comprising an excitation light source for emitting excitation light for exciting the liquid, and wherein the optical fiber unit further includes an excitation light guiding portion for guiding the excitation light emitted from the excitation light source toward the detecting end, the liquid held in the inner hollow space emitting the light upon being irradiated with the excitation light.

3. A device of claim 2, wherein the optical fiber unit is constructed from a pair of optical fibers, the pair of optical fibers being connected along their end sections to form a Y-shape consisting of a trunk portion and a first and a second branch portions, the trunk portion being formed from the connected lengths of the pair of optical fibers and having the detecting end, the first branch portion being formed from the remaining length of one of the pair of optical fibers and connected to the optically-measuring unit, the second branch portion being formed from the remaining length of the other one of the pair of optical fibers and connected to the excitation light source.

4. A device of claim 3, wherein the optically-measuring unit includes a light selecting unit for selecting the light emitted from the liquid from the excitation light.

5. A device of claim 1, wherein the air suction unit is connected with the inner hollow space via a gap formed in the inside of the optical fiber unit.

6. A device of claim 5, wherein the optical fiber unit is formed from a bundle of a plurality of optical fibers, the inner hollow space being communicated with a gap formed between the plurality of optical fibers, the air suction unit being connected to the gap.

7. A device of claim 1, wherein the air suction unit is connected with the inner hollow space via a gap formed in the outside of the optical fiber unit.

8. A device of claim 7, further comprising a tubular jig member integrally formed with the tip member, the tubular jig member having an inner peripheral wall defining an inner hollow portion through which the optical fiber unit is inserted so as to expose the detecting end thereof into the inner hollow space of the tip member, a gap being formed between an outer peripheral surface of the optical fiber unit and the inner peripheral surface of the jig member, the gap being communicated with the inner hollow space in the tip member, the air suction unit being connected to the gap.

9. A device of claim 1, wherein the sucking condition control unit includes a sucking amount control unit for controlling the sucking amount.

10. A device of claim 1, wherein the sucking condition control unit includes a sucking speed control unit for controlling the sucking speed.

11. A device of claim 1, wherein the sucking condition control unit includes a sucking timing control unit for controlling the sucking timing.

* * * * *